(12) United States Patent
Röder

(10) Patent No.: US 11,986,414 B2
(45) Date of Patent: May 21, 2024

(54) CUFF FOR ORTHOTIC TREATMENT

(71) Applicant: Ulrike Röder, Lüneburg (DE)

(72) Inventor: Harry Röder, Soderstorf (DE)

(73) Assignee: Ulrike Röder, Melbeck (DE)

( * ) Notice: Subject to any disclaimer, the term of this patent is extended or adjusted under 35 U.S.C. 154(b) by 741 days.

(21) Appl. No.: 15/940,889

(22) Filed: Mar. 29, 2018

(65) Prior Publication Data

US 2018/0280179 A1   Oct. 4, 2018

(30) Foreign Application Priority Data

Mar. 30, 2017   (DE) .......................... 202017101866

(51) Int. Cl.
*A61F 5/01* (2006.01)
*A61F 13/10* (2006.01)
*A61F 13/06* (2006.01)

(52) U.S. Cl.
CPC .......... *A61F 5/0109* (2013.01); *A61F 5/0118* (2013.01); *A61F 13/10* (2013.01);
(Continued)

(58) Field of Classification Search
CPC ........ A61F 5/01; A61F 5/0102; A61F 5/0104; A61F 5/0118; A61F 5/013; A61F 5/0106; A61F 5/0109; A61F 5/0111; A61F 5/0123; A61F 5/0193; A61F 5/026; A61F 5/03; A61F 5/058; A61F 5/05825; A61F 5/0585; A61F 5/05858; A61F 5/05866; A61F 5/37; A61F 5/3715; A61F 5/3723;
(Continued)

(56) References Cited

U.S. PATENT DOCUMENTS 1,462,534 A * 7/1923 Condylis et al. ..... A61F 13/066
602/66
1,717,609 A * 6/1929 Ludwig ................. A61F 13/066
602/66
(Continued)

FOREIGN PATENT DOCUMENTS

DE   3625983 A1   2/1988
DE   4137381 A1   5/1993
(Continued)

*Primary Examiner* — Ophelia A Hawthorne
*Assistant Examiner* — Michael Milo
(74) *Attorney, Agent, or Firm* — Thomas M. Freiburger

(57) ABSTRACT

The invention relates to a cuff for orthotic treatment of joint or muscle pains in the region of joints of the human or animal body, which as a cross cuff has a first cuff part (1) for application on a first body part below the joint and a second cuff part (2) for application on a second body part above the joint, wherein the two cuff parts are joined to one another by means of a connection region (3) and in each case are formed from a belt that is provided with fastening means and may be laid around the respective body part, wherein the connection region (3) between the two cuff parts on placement of the cuff on the body in the region of the inside of the joint impedes extension of the first body part with respect to the second body part, in that the connecting region is displaced under tensile stress. According to the invention, at least one partial region (4) of the second cuff part (2) above the joint is made to be stretchable (FIG. 1).

7 Claims, 7 Drawing Sheets

Figure 1:
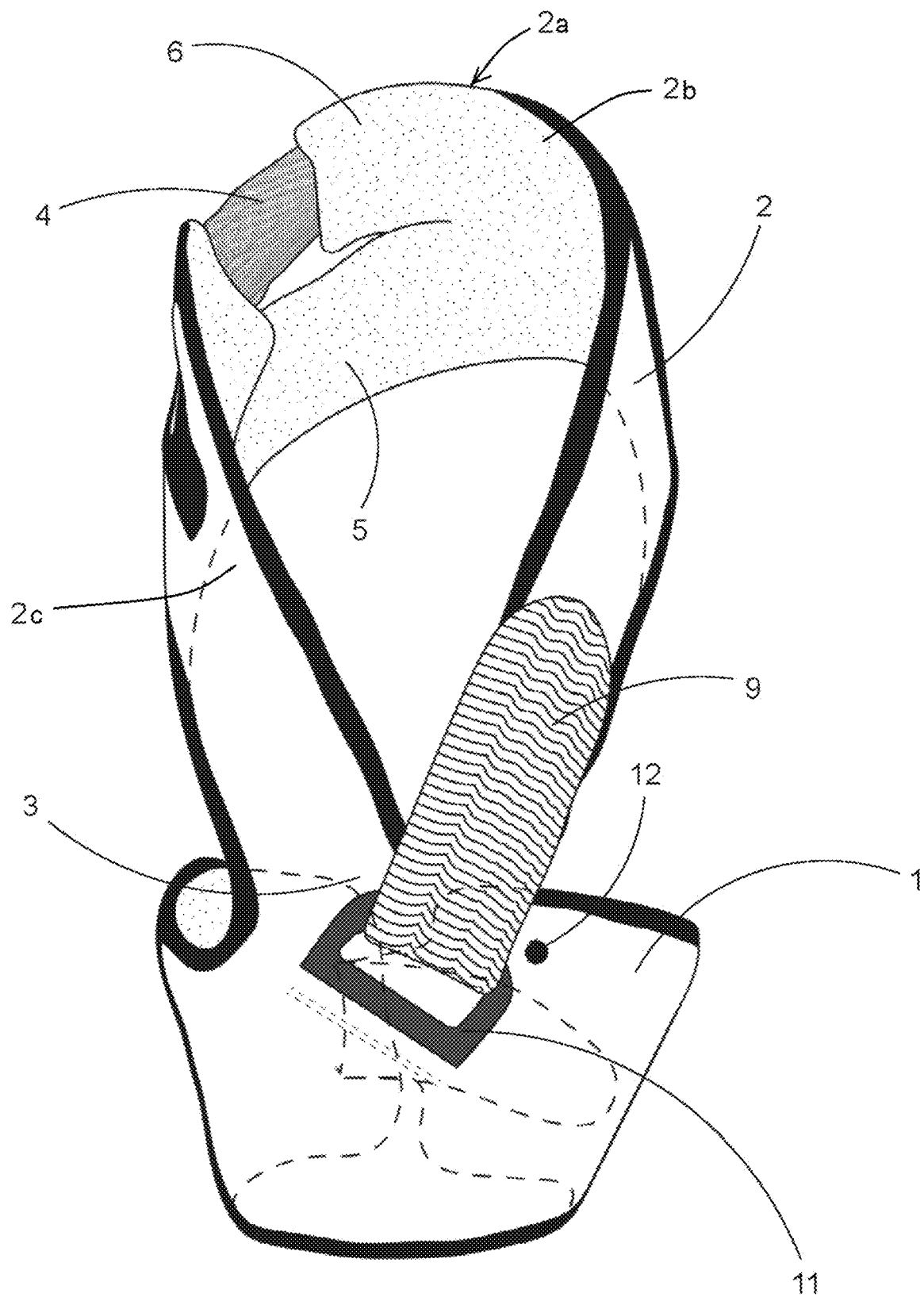

(52) U.S. Cl.
CPC .......... *A61F 13/102* (2013.01); *A61F 13/108* (2013.01); *A61F 13/062* (2013.01)

(58) Field of Classification Search
CPC .... A61F 5/3738; A61F 5/3746; A61F 5/3753; A61F 5/3769; A61F 5/3776; A61F 13/06; A61F 13/061; A61F 13/062; A61F 13/065; A61F 13/066; A61F 13/08; A61F 13/085; A61F 13/10; A61F 13/101; A61F 13/102; A61F 13/108
See application file for complete search history.

(56) References Cited

U.S. PATENT DOCUMENTS

| | | | | |
|---|---|---|---|---|
| 3,118,443 | A * | 1/1964 | Dykinga | A61H 1/0218 |
| | | | | D29/101.1 |
| 4,598,703 | A * | 7/1986 | Lindemann | A61F 5/3738 |
| | | | | 602/20 |
| 4,735,198 | A * | 4/1988 | Sawa | A61F 13/146 |
| | | | | 128/878 |
| 4,807,607 | A * | 2/1989 | Roder | A61F 5/0118 |
| | | | | 602/20 |
| 5,403,268 | A * | 4/1995 | Clement | A61F 5/3738 |
| | | | | 602/20 |
| 5,425,702 | A * | 6/1995 | Carn | A61F 13/00059 |
| | | | | 602/76 |
| 5,792,091 | A * | 8/1998 | Staudinger | A61F 5/0118 |
| | | | | 602/57 |
| 5,928,172 | A * | 7/1999 | Gaylord | A61F 5/0118 |
| | | | | 602/21 |
| 2004/0193082 | A1* | 9/2004 | Cofre | A61F 5/3738 |
| | | | | 602/4 |
| 2005/0121041 | A1* | 6/2005 | Barnitz | A61F 5/3723 |
| | | | | 128/869 |
| 2007/0100265 | A1* | 5/2007 | Gamada | A61F 5/0123 |
| | | | | 602/26 |

FOREIGN PATENT DOCUMENTS

| | | |
|---|---|---|
| EP | 0255881 A1 | 2/1988 |
| EP | 2651349 B1 | 10/2017 |
| WO | WO-2016119798 A1 * | 8/2016 |

\* cited by examiner

CUFF FOR ORTHOTIC TREATMENT

BACKGROUND OF THE INVENTION

This application claims priority from German patent application number DE 202017101866.0, filed Mar. 30, 2017.

The invention relates to a cuff for orthotic treatment of joint or muscle pain in joints of the human or animal body in accordance with the preamble of claim 1.

It is known to alleviate or eliminate joint or muscle pains that arise in the region of an elbow or knee joint, frequently due to overuse or continuous stress, by using a cross cuff.

It is essential in this treatment method that an effect occurs only when the arm or leg extension in the boundary region of the extension is either entirely prevented or at least rendered more difficult.

Known cuffs used for this purpose consist as a rule of two cuff parts, one of which when used on an arm encloses the forearm and a second part the upper arm, wherein the two parts are joined to one another in a transition region. Especially the partial region enclosing the forearm must be in a conical design so as to be able to follow the arm surface as closely as possible. The size of the cuff to be used depends on the body size, in particular the arm diameter. For exact fitting on the body, the cuff is provided with fastening means, which frequently are designed as buckles with hinge pins. In this way the diameter of the cuff parts can be adjusted to the arm diameter.

EP 0 255 881 A1 discloses a corresponding bandage for treatment of forearm pain. With this bandage, which is made of skin-friendly leather, a collar is placed around the forearm and secured in diameter by a buckle. On the upper edge of the collar there is a second collar secured in the shape of a loop, which is placed around the forearm and forms a traction belt between lower and upper collar. On arm extension, the traction belt between the lower and upper collar impedes full extension of the arm and thereby relieves the joint in the extended state.

Since the connecting region between the upper and lower collar forms the traction belt and the upper collar is formed as a loop, it is sometimes difficult to place the upper collar adequately securely on the upper arm so as to prevent slipping. If the application is too tight, however, wearing comfort is limited. Further, the wearing position of the upper arm collar changes with the angular position between the upper arm and forearm, so that there can easily be pinching at one edge of the upper arm collar.

It is therefore the object of the invention to improve wearing comfort of a cuff for orthotic treatment of joint or muscle pain in the region of joints of the human or animal body in such a way that misalignments of the cuff with respect to placement on the body can be avoided and handling can be improved.

This object is achieved by the invention of claim 1. Further embodiments of the invention are specified in the subclaims.

The invention is based on a cuff as specified in EP 0 255 881 A1. According to the invention, at least a partial region of the second cuff part to be arranged above the joint is stretchable.

The stretchability of the second cuff part results in the angular position of the second cuff part being adjusted to the respective angular position between the body parts below and above the joint. This considerably improves wearing comfort and pinching of the upper arm on edges of the cuff part is avoided, so that blood flow in the upper arm is also not impaired.

Preferably, the stretchable partial region extends transversely over the second cuff part, so that the entire rear region of the second cuff part is flexible.

In a further developed embodiment, the stretchable partial region can also be formed from two or more separate band-like strands of the second cuff portion, of which one or more of the strands facing away from the joint flexure have a rubber elastic design, wherein in each case the other strand is not longitudinally elastic, so as to be able to maintain the tension force of the second cuff portion.

The inside of the cuff parts preferably comprises a layer of textile, skin-friendly material, in particular velour fabric. The outside of the cuff can be provided over the entire surface with high-tensile-strength loop tape, which forms the counterpart to the VELCRO hook and loop fastener when using VELCRO closures.

The cuff contains as few as possible buckles or other fastening parts, which may protrude from the cuff surface. For deflecting the hook-and-loop fastening tabs, preferably flat D-shaped rings or annular eyelets are used. Alternatively thereto, caps in the cuff parts can be used, through which the fastening tabs can be passed.

The insides of the cuff parts can also have comfort-enhancing cushions as well as pads, which can exert an increased pressure force on specific body part regions.

In order to give the user clear instruction on how to apply the cuff, it preferably has marking that specifies that the cuff is to be applied in such a way that the marking is in the region of the elbow flexure.

Below the invention is explained in more detail with reference to the drawings using an exemplary embodiment.

Figure 2:
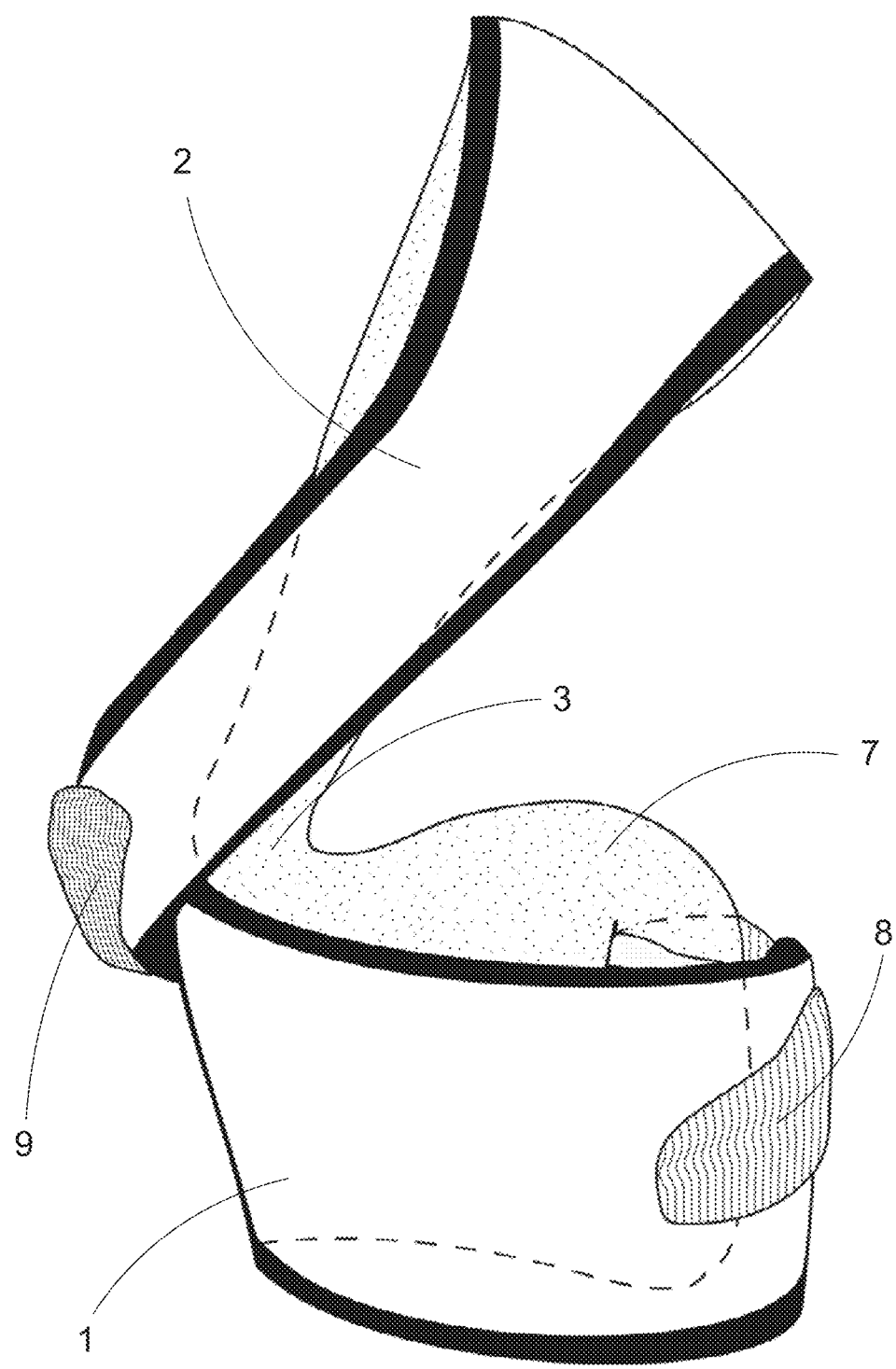
Figure 3:
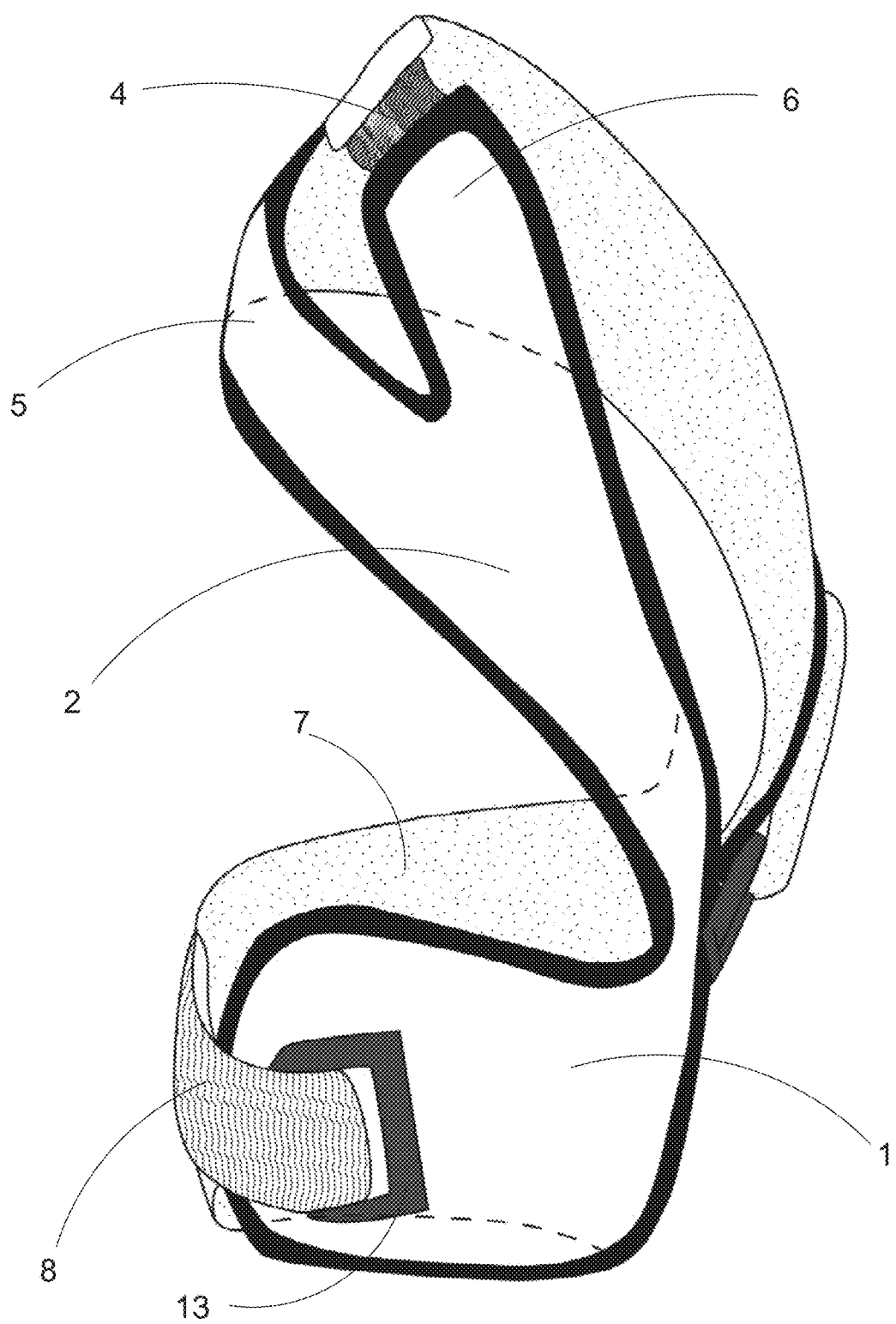
Figure 4:
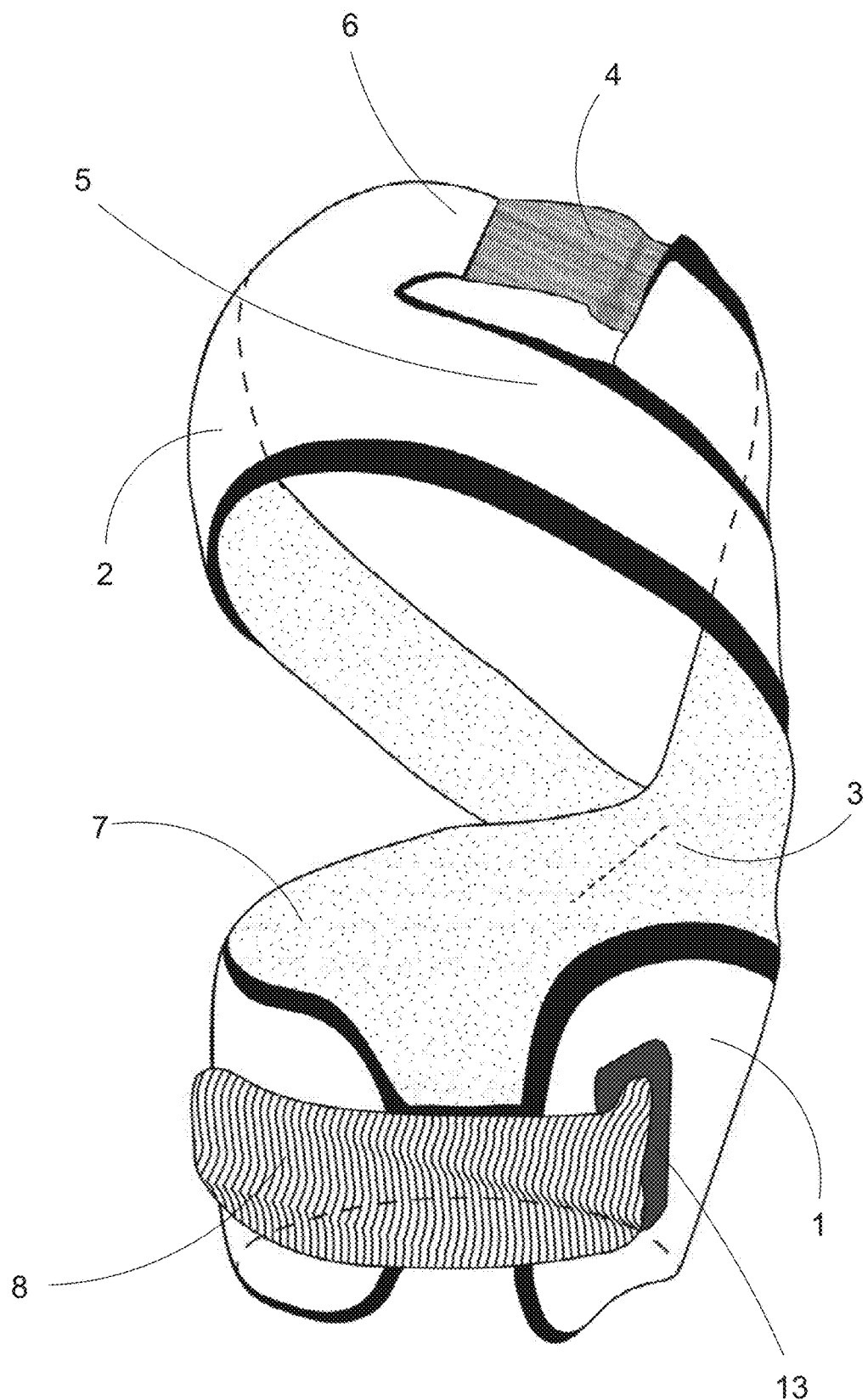
Figure 5:
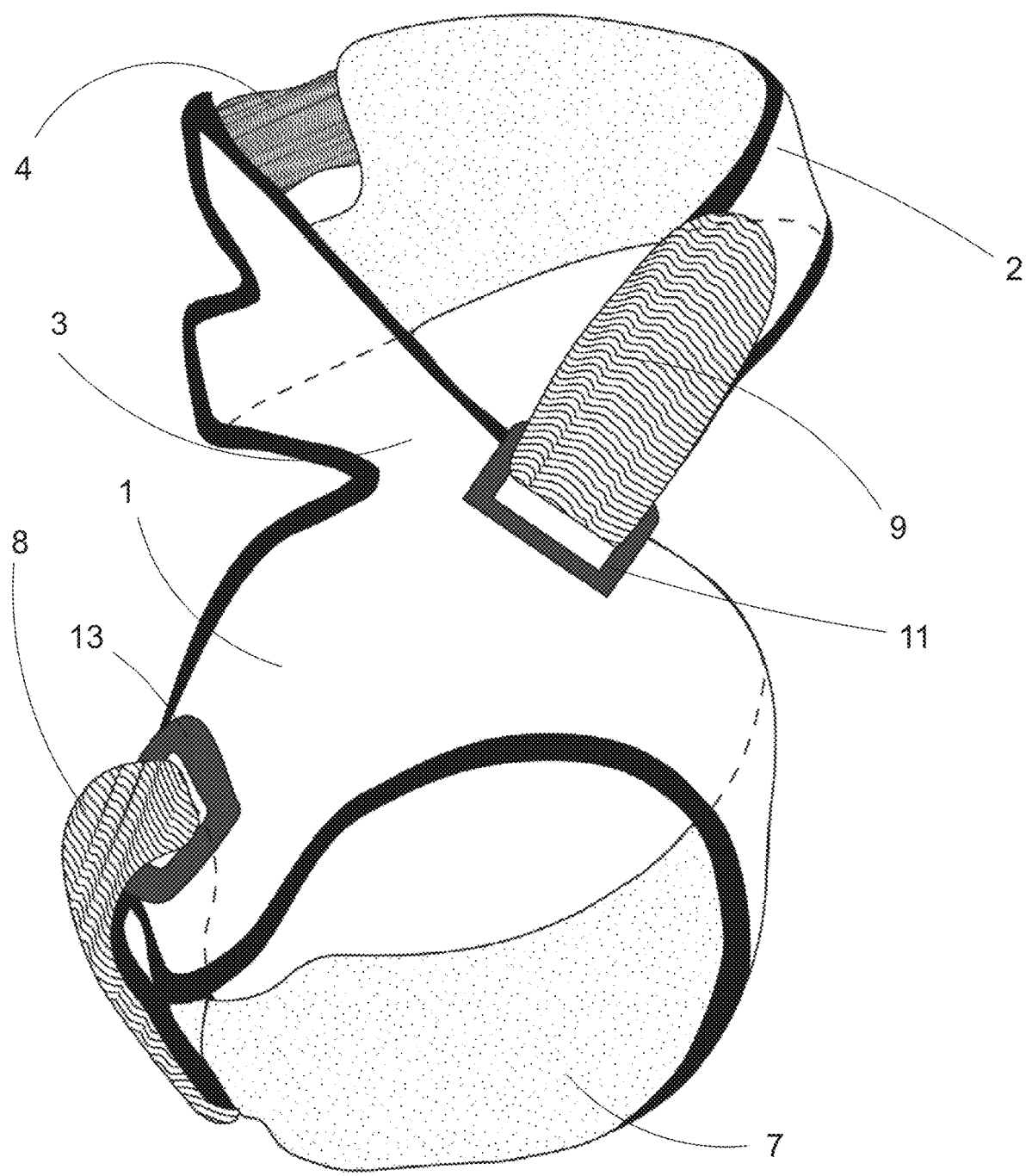
Figure 6:
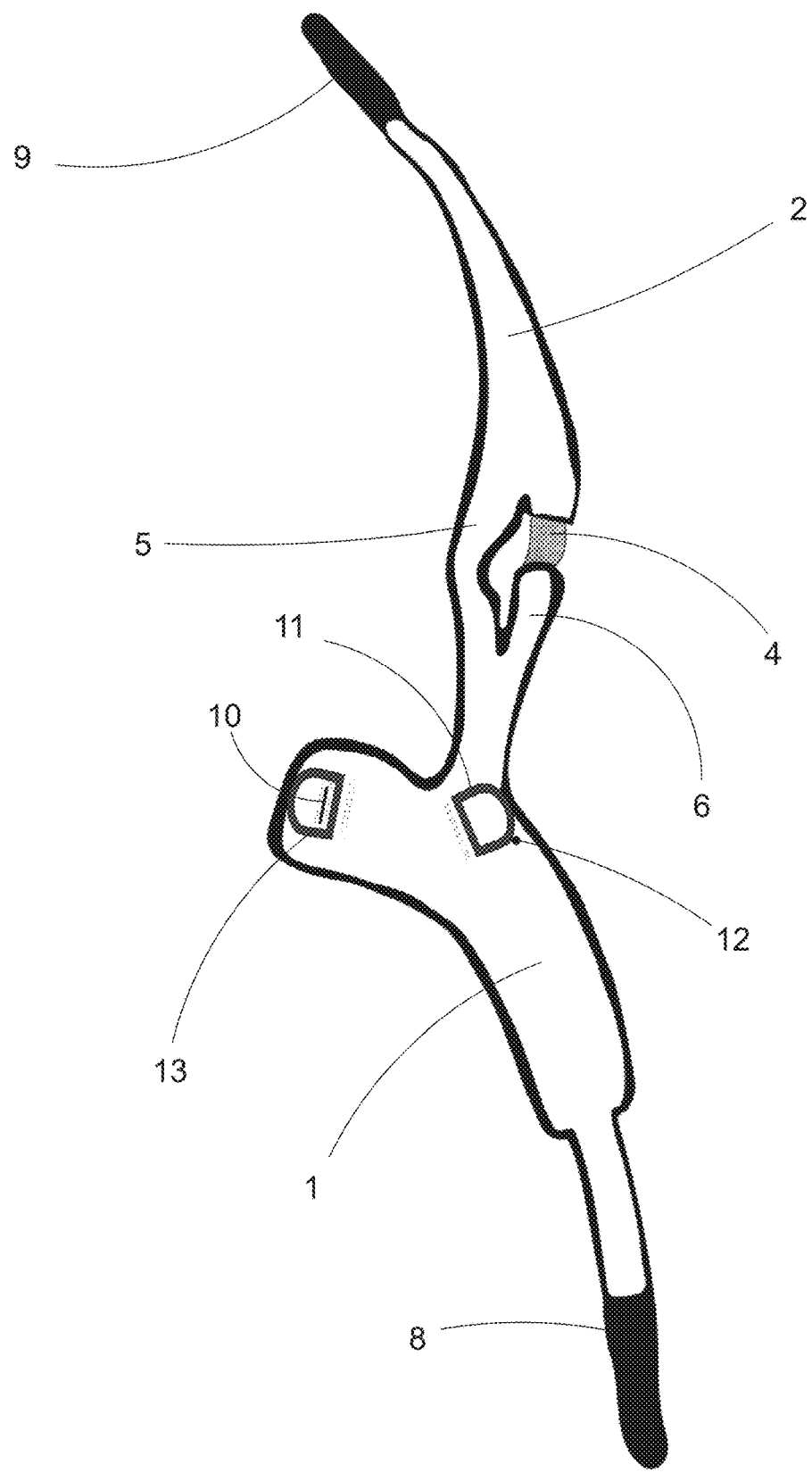
Figure 7:
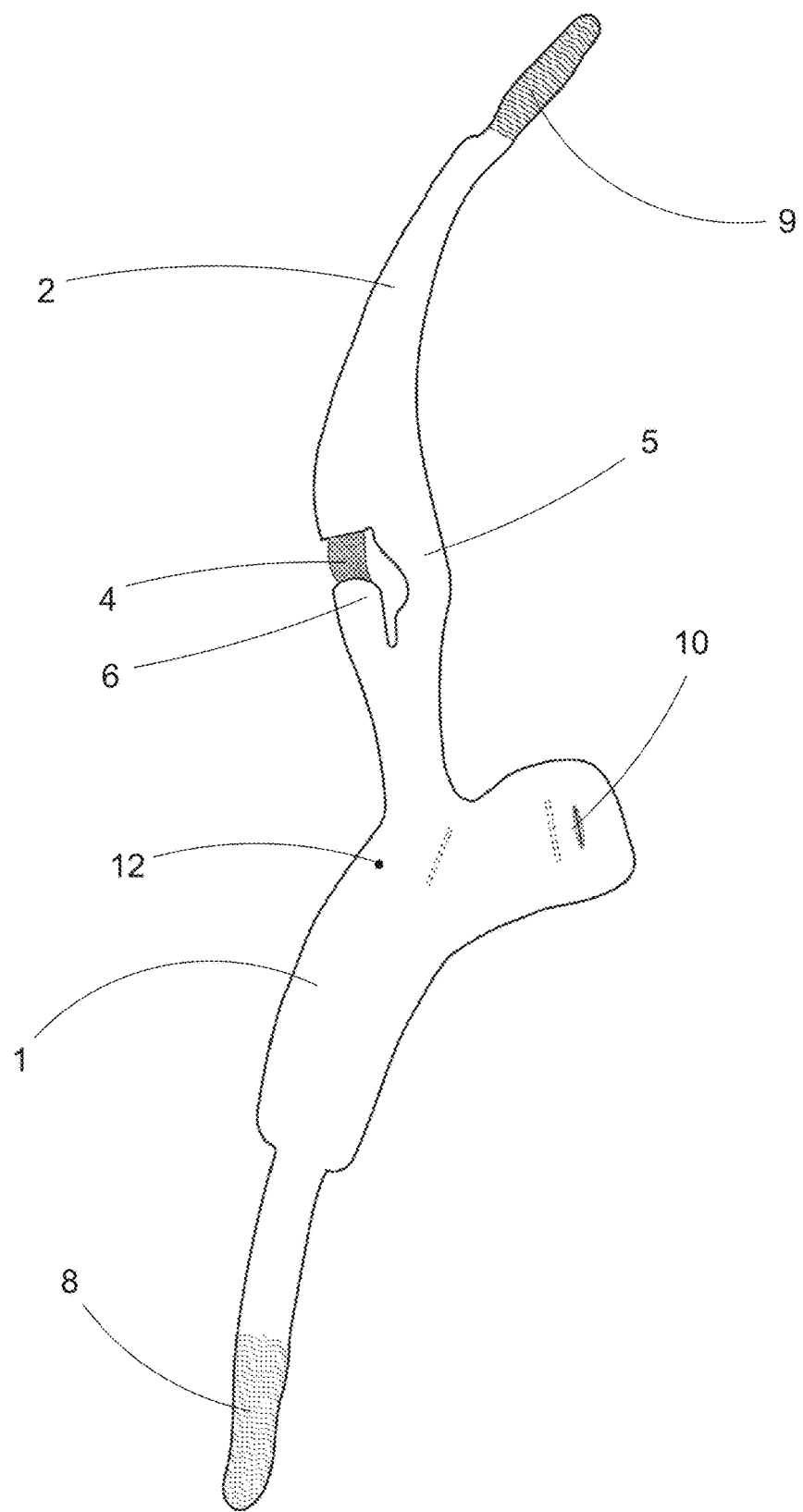

Wherein:

FIG. 1 a front view of a cuff,
FIG. 2 a first side view of a cuff,
FIG. 3 a second side view of a cuff,
FIG. 4 a rear view of a cuff,
FIG. 5 an oblique bottom view of a cuff,
FIG. 6 a front view of a flattened cuff, and
FIG. 7 a rear view of a flattened cuff.

The cuff according to FIG. 1 in the exemplary embodiment serves to support an elbow joint. A first cuff part 1 with a conical shape is hereby pushed onto the forearm, somewhat below the elbow joint. A loop-shaped second cuff part 2 encloses the upper arm. The two cuff parts are joined to one another in the connecting region 3. In practical application this region is in the region of the elbow flexure. In order to establish a precise position of the cuff, a marking 12, visible as a colored point-form marking on the first cuff part, should be located in the region of the elbow flexure.

The two cuff parts are formed integrally with one another. The loop forming the second cuff part 2 is fixedly secured at one end to the first cuff part 1. The second end of the second cuff part 2 has an adhesive or VELCRO hook and loop fastener closure 9, whose tab-shaped end is passed through a D-shaped ring 11, which is secured to the first cuff part 1. The end of the second cuff part 2 can thereby be fixed by the hook and loop closure in different positions.

The second cuff part 2, which is placed around the upper arm, is divided in the upper region into two longitudinally running strands 5 and 6, that form a flexible portion 2a of the second cuff part, the ends of the flexible portion being connected to remaining areas 2b and 2c of the second cuff part. Whereas strand 5 is longitudinally stable, strand 6 has a partial region 4 which is designed to be longitudinally elastic. The partial region 4 can be formed as a rubber elastic band. The different longitudinal elasticity of strands 5 and 6 results in the advantage that different angular positions of the second cuff part 2 with respect to the upper arm can be compensated without problems, as the pressure force which is exerted by the second cuff part 2 on the forearm is largely independent of the angular position with regard to the upper arm. This avoids a situation in which the partial region 4, in an acute angular position with respect to the upper arm longitudinal axis, presses too forcefully on the upper arm, and in this respect can cause discomfort or pressure sores.

FIG. 2. shows the cuff in a side view. This figure serves in particular to demonstrate the arrangement of the VELCRO hook and loop fastener closures 8 and 9. The VELCRO hook and loop fastener closure 9 is formed in accordance with FIG. 1. Likewise the first cuff part is provided with a VELCRO closure 8, by means of which the diameter of the first cuff part can be set. In this representation, the second cuff part is shown without showing strands 5 and 6.

FIG. 3 shows a second side view of the cuff, in which the arrangement of the strands 5 and 6 with the longitudinally elastic partial region 4 formed in strand 6 is presented.

FIG. 4 shows a rear view with the VELCRO closure 8, whose tab is passed through a slotted opening 10 (FIG. 7) at the other end of the first cuff part. If the opening 10 has sufficient edge reinforcement, it is not necessary to use additional fastening elements. However, the opening 10 can also be reinforced by an additional D-shaped ring 13 or an annular eyelet.

The inside of the cuff is preferably covered with a textile material, in particular velour 7, which has pleasant wearing properties. The outside of the cuff can be covered with a loop tape, which is the counterpart to the Velour closure, so that the VELCRO closure tabs can be secured at every point on the outside of the cuff.

FIG. 5 shows a bottom view for further visualization of the cuff.

FIG. 6 shows a flattened cuff. At one end of the first cuff part 1 is the VELCRO closure 8, and at the other end the opening 10 reinforced with a D-shaped ring 13. The figure clearly shows that the second cuff part 2 is securely joined to the first cuff part 1. The two cuff parts may be integrally formed, but for manufacturing reasons it may also be provided that the two cuff parts are connected by means of a seam connection. The figure also clearly shows the arrangement of the flexible partial region 4 in the strand 6, whereas the strand 5 is not formed to be longitudinally elastic. The adhesive or VELCRO closure 9 is passed through the D-shaped ring 13 when used.

FIG. 7 shows a corresponding view from FIG. 6 in a rear view.

The design of the cuff from longitudinally stable material (except for the partial region 4) allows simple and secure placement on an arm, in particular an elbow. When the cuff is flattened out, it can be stored or shipped in a space-saving arrangement. Placement on the arm can be done with one hand, as there is no need for complicated threading through buckles with hinge pins or the like. hook and loop closures that are used are flexibly configurable and adjustable even when in place.

REFERENCE SYMBOLS 1 first cuff part
2 second cuff part
3 connecting region
4 partial region
5 strand
6 strand
7 Velour fabric
8 adhesive or hook/loop closure
9 adhesive or hook/loop closure
10 opening
11 ring
12 marking
13 ring

The invention claimed is:

1. An orthotic cuff for orthotic treatment of joint or muscle pains in the region of joints of the human or animal body, including an elbow joint, which as a cross cuff has a first cuff part (1) for placement on a first body part below the joint, adapted for a lower arm below an elbow joint, and a second cuff part (2) for placement on a second body part above the joint, adapted for an upper arm above the elbow joint, wherein the two cuff parts are joined to one another by means of a connecting region (3) without a pivot joint, and in each case are formed from a belt that is provided with a fastening means (8, 9) and is configured to be laid around the respective lower and upper arm, wherein the connecting region (3) between the two cuff parts upon application of the orthotic cuff on the body in a region of an inside of the joint impedes extension of the lower arm with respect to the upper arm, in that the connecting region (3) is displaced under tensile stress, characterized in that a flexible portion has two ends connected to two separate remaining areas of the second cuff part, extending transversely over the second cuff part (2) and is formed from two or more separate parallel band-shaped strands (5, 6) running in longitudinal direction of the second cuff part (2), wherein at least one strand (5) is configured as being non-stretchable in longitudinal direction and is integrally formed with same material of said remaining areas of the second cuff part, and another strand (6), configured to face away from the joint flexure when worn, has a length formed in part of non-stretchable material and in part (4) from elastic rubbery material stretchable in longitudinal direction of the second cuff part, remaining areas of the second cuff part being flexible but not stretchable, both the strands (5, 6) being in fixed parallel position relative to one another and positioned to be on an outer side of the elbow joint when worn, the non-stretchable second cuff part being effective to restrain slippage of the second cuff part toward the elbow joint when the lower arm is fully extended relative to the upper arm.

2. The orthotic cuff according to claim 1, characterized in that the fastening means are designed as configurable adhesive or hook-and-loop closures (8, 9), wherein in each case a tab of a first end of the respective cuff part can be passed through an annular eyelet or a D-shaped ring (11, 13) or an opening (10) on a second end of the respective cuff part, and may be connected to itself or a surface part of the respective cuff part.

3. The orthotic cuff according to claim 2, characterized in that the ring (11) or the opening (10) for fastening of the second cuff part (2) to the first cuff part (1) in the connecting region (3) is between the first and second cuff part.

4. The orthotic cuff according to claim 1, characterized in that the first and second cuff parts on an inner side contain a layer made of Velour fabric (7).

5. The orthotic cuff according to claim 1, characterized in that an outer surface of the first and second cuff parts (1, 2) is designed as a high tensile-strength loop tape at least in part.

6. The orthotic cuff according to claim 1, characterized in that the first cuff part (1) has an outside marking (12) for specifying a location of the connecting region in a region of joint flexure.

7. The orthotic cuff according to claim 1, characterized in that said other strand of elastic rubbery material is at an upper position of the second cuff part, above the non-stretchable strand.

* * * * *